US012690886B2

(12) United States Patent
Munim

(10) Patent No.: US 12,690,886 B2
(45) Date of Patent: Jul. 28, 2026

(54) INTRODUCER AND/OR CANNULATION NEEDLE AND METHODS OF MAKING AND USING THE SAME

(71) Applicant: Amjad Munim, Fort Lauderdale, FL (US)

(72) Inventor: Amjad Munim, Fort Lauderdale, FL (US)

( * ) Notice: Subject to any disclaimer, the term of this patent is extended or adjusted under 35 U.S.C. 154(b) by 1115 days.

(21) Appl. No.: 17/740,436

(22) Filed: May 10, 2022

(65) Prior Publication Data

US 2022/0354535 A1     Nov. 10, 2022

Related U.S. Application Data

(60) Provisional application No. 63/186,310, filed on May 10, 2021.

(51) Int. Cl.
*A61B 17/34* (2006.01)
*A61M 5/158* (2006.01)

(52) U.S. Cl.
CPC ...... *A61B 17/3415* (2013.01); *A61B 17/3421* (2013.01); *A61M 5/158* (2013.01)

(58) Field of Classification Search
CPC ........... A61B 17/3415; A61B 17/3421; A61M 5/158; A61M 25/065
See application file for complete search history.

(56) References Cited

U.S. PATENT DOCUMENTS

| | | | | |
|---|---|---|---|---|
| 2,211,537 A | * | 8/1940 | Dickinson | ................ B21G 1/08 |
| | | | | 29/520 |
| 5,190,528 A | | 3/1993 | Fonger et al. | |
| 5,222,502 A | * | 6/1993 | Kurose | ............ A61B 5/150732 |
| | | | | 600/584 |

| | | | | |
|---|---|---|---|---|
| 5,284,476 A | * | 2/1994 | Koch | .................. A61F 9/00736 |
| | | | | 606/166 |
| 5,289,919 A | * | 3/1994 | Fischer | .................. A61C 19/02 |
| | | | | 206/459.5 |
| 6,135,984 A | * | 10/2000 | Dishler | ............... A61M 3/0279 |
| | | | | 606/162 |
| 6,413,245 B1 | * | 7/2002 | Yaacobi | ................ A61F 9/0017 |
| | | | | 604/521 |
| 7,153,316 B1 | * | 12/2006 | McDonald | ............ A61F 9/0133 |
| | | | | 606/166 |
| 7,462,184 B2 | | 12/2008 | Worley et al. | |
| 9,585,692 B2 | * | 3/2017 | Kurth | ................. A61B 17/3468 |

(Continued)

OTHER PUBLICATIONS

PCT International Search Report and Written Opinion.
PCT International Search Report on Patentability.

*Primary Examiner* — Theodore J Stigell

(74) *Attorney, Agent, or Firm* — Ashley D. Johnson; Dogwood Patent and Trademark Law

(57) ABSTRACT

The presently disclosed subject matter is directed to a vein introducer and/or cannulation needle. Specifically, the needle includes a straight section attached to a distal end of a housing, and a curved section that comprises sharp tip. The curved or arcuate section is shaped to facilitate vessel introduction and maneuverability. Thus, the curved shape of the needle allows a user to access an internal vessel (e.g., a subclavian vein) in a parallel manner. As a result, the vessel can be accessed more safely and with decreased pain. The disclosed needle can therefore be used to provide fluidic and/or instrument access to an internal body structure (e.g., a subclavian vein).

15 Claims, 11 Drawing Sheets

(56)         References Cited

U.S. PATENT DOCUMENTS

2002/0077520 A1 *  6/2002  Segal ................... A61N 5/1015
                                             600/1
2006/0161177 A1     7/2006  Worley et al.
2018/0264201 A1 *   9/2018  Weksel ............... A61M 5/3286

* cited by examiner

My Introducer/Cannulation Needle (Resultant Long Axis Approach)

Rt. Subclavian Artery

Brachial Plexus

Rt. IJ Vein

Anterior Scalene Muscle

Clavicle

Rt. Subclavian Vein

Apex of Rt. Lung

2nd Rib

3rd Rib

Rt. Axillary Vein

Rt. Lung

INTRODUCER AND/OR CANNULATION NEEDLE AND METHODS OF MAKING AND USING THE SAME

CROSS-REFERENCE TO RELATED APPLICATIONS

This application claims priority to U.S. Provisional Patent Application No. 63/186,310, filed May 10, 2021, the entire content of which is hereby incorporated by reference.

TECHNICAL FIELD

The presently disclosed subject matter is generally directed to an introducer and/or cannulation needle, such as for use with the subclavian vein. The presently disclosed subject matter further includes methods of making and using the disclosed needle.

BACKGROUND

Approximately five million surgical procedures per year in the United States require a needle to be advanced into the subclavian vein. Once inserted, the needle can be used for a variety of purposes, such as to place a central venous catheter, to administer fluids and medications, blood pressure monitoring, hemodialysis, pacemaker insertions, long term medication administration, nutrition administration, Swan-Ganz catheter placement, and the like. Conventionally, straight needles are used to access the subclavian vein. However, these prior art needles suffer from several drawbacks. Specifically, the linear shape results in the needle being directed at the vessel wall (not along the long axis of the vein), thereby increasing the risk of penetrating nearby structures. In addition, subclavian veins are not well visualized on ultrasound, such that cannulation attempts are typically blind. The vein is not superficial to the skin, having a depth of about 2.5-3 centimeters. Further, as the vein passes underneath the clavicle it changes course and extends further into the tissue, curving and advancing toward the pleura and ipsilateral lung until it joins the internal jugular vein behind the clavicle and manubrium. The pleura and lung, subclavian artery, thoracic duct, first rib, and intercostal muscles, and certain nerves are positioned very close to the subclavian vein throughout its course. Accordingly, these structures are vulnerable during cannulation due to their extreme proximity, especially the lung. Thus, if a straight needle is inserted too far into the body and/or at an incorrect angle, the needle can easily puncture the lung or other nearby structure. It would therefore be beneficial to provide an introducer and/or cannulation needle that overcomes the shortcomings of the prior art to provide safer and more efficient insertion into a vessel (such as the subclavian vein).

SUMMARY

In some embodiments, the presently disclosed subject matter is directed to a tubular needle comprising a housing defined by a housing proximal end and a housing distal end, wherein the housing proximal end includes a connector. The needle further includes a straight section comprising a proximal end and a distal end, the proximal end operably connected to the housing distal end. Further, the needle includes a curved section comprising a proximal end and a distal end, wherein the proximal end is operably connected to the distal end of the straight section, and wherein the distal end of the curved section comprises a sharpened tip.

In some embodiments, the connector comprises a series of screw threads.

In some embodiments, the straight section has a length of about 0.1-1 inches and the curved section has a length of about 0.1-5 inches.

In some embodiments, the curved section comprises a central angle of about 150-270 degrees.

In some embodiments, the curved section is configured in a segment of a circle, a segment of an ellipse, or a segment of a parabola.

In some embodiments, the curved section comprises about 40-90 percent of a total length of the tubular needle, the straight section comprises as about 5-50 percent of the total length of the tubular needle, and the housing comprises about 5-50 percent of the total length of the tubular needle.

In some embodiments, the needle is configured within a kit comprising a plurality of tubular needles of various sizes and shapes.

In some embodiments, the straight section, curved section, or both are constructed from stainless steel, nitinol, tantalum, cobalt, chrome, titanium, nickel, and/or combinations or alloys thereof.

In some embodiments, the presently disclosed subject matter is directed to a method of accessing a target vessel. Particularly, the method comprises positioning a tubular needle at a target location on a patient. The tubular needle comprises a housing defined by a housing proximal end and a housing distal end, wherein the housing proximal end includes a connector; a straight section comprising a proximal end and a distal end, the proximal end operably connected to the housing distal end; a curved section comprising a proximal end and a distal end, wherein the proximal end is operably connected to the distal end of the straight section, and wherein the distal end of the curved section comprises a sharpened tip. The method includes advancing the tip of the needle into the interior of the patient and maneuvering the curved section of the needle inside the patient facilitate placement along the long axis of the target vessel, whereby the target vessel is accessed.

In some embodiments, the target vessel is a subclavian vein.

In some embodiments, the curved section comprises a central angle of about 150-270 degrees.

In some embodiments, the vessel is accessed to withdraw blood, place a central venous catheter, administer fluids, administer medication, monitor blood pressure, perform hemodialysis, insert a medical device, or combinations thereof.

In some embodiments, the presently disclosed subject matter is directed to a method of treating a patient by accessing a target vessel. Specifically, the method comprises positioning a tubular needle at the target location on the patient. The tubular needle comprises a housing defined by a housing proximal end and a housing distal end, wherein the housing proximal end includes a connector; a straight section comprising a proximal end and a distal end, the proximal end operably connected to the housing distal end; a curved section comprising a proximal end and a distal end, wherein the proximal end is operably connected to the distal end of the straight section, and wherein the distal end of the curved section comprises a sharpened tip. The method includes advancing the tip of the needle into the interior of the patient and maneuvering the curved section of the needle inside the patient to facilitate placement along the long axis of the target vessel, wherein the patient is treated by accessing the vessel.

In some embodiments, the treating comprises withdrawing blood, inserting a central venous catheter, administering fluids, administering medication, monitoring blood pressure, performing hemodialysis, inserting a medical device, or combinations thereof.

In some embodiments, the curved section comprises a central angle of about 150-270 degrees.

BRIEF DESCRIPTION OF THE DRAWINGS

FIG. 4b is a cross-sectional side plan view a circular curved needle section in accordance with some embodiments of the presently disclosed subject matter.

FIG. 4c is a cross-sectional side plan view an elliptical curved needle section in accordance with some embodiments of the presently disclosed subject matter.

DETAILED DESCRIPTION

Figure 1:
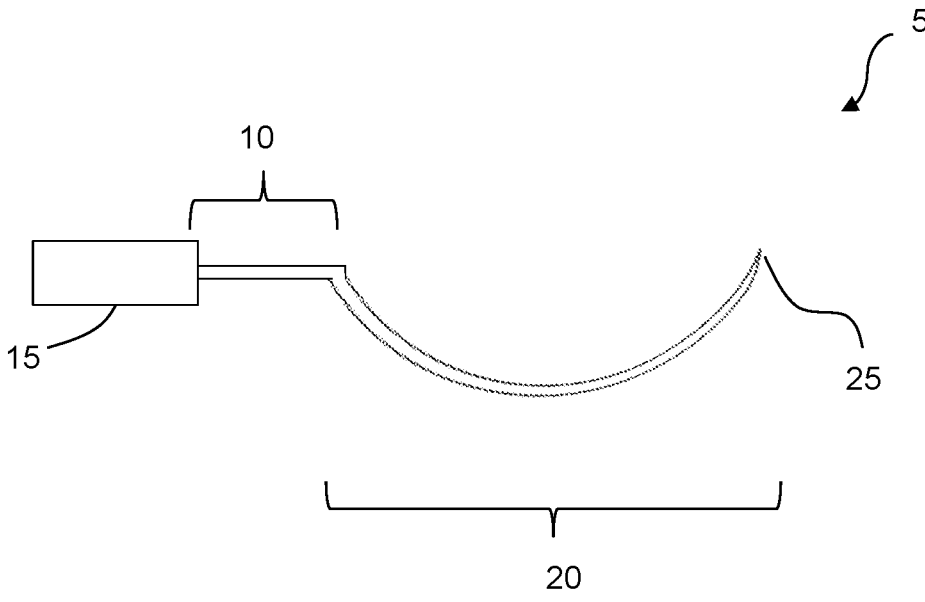
FIG. 1 is a side plan view of an introducer or cannulation needle in accordance with some embodiments of the presently disclosed subject matter.

The presently disclosed subject matter is introduced with sufficient details to provide an understanding of one or more particular embodiments of broader inventive subject matters. The descriptions expound upon and exemplify features of those embodiments without limiting the inventive subject matters to the explicitly described embodiments and features. Considerations in view of these descriptions will likely give rise to additional and similar embodiments and features without departing from the scope of the presently disclosed subject matter.

Unless defined otherwise, all technical and scientific terms used herein have the same meaning as commonly understood to one of ordinary skill in the art to which the presently disclosed subject matter pertains. Although any methods, devices, and materials similar or equivalent to those described herein can be used in the practice or testing of the presently disclosed subject matter, representative methods, devices, and materials are now described.

Following long-standing patent law convention, the terms "a", "an", and "the" refer to "one or more" when used in the subject specification, including the claims. Thus, for example, reference to "a device" can include a plurality of such devices, and so forth. It will be further understood that the terms "comprises," "comprising," "includes," and/or "including" when used herein specify the presence of stated features, integers, steps, operations, elements, and/or components, but do not preclude the presence or addition of one or more other features, integers, steps, operations, elements, components, and/or groups thereof.

Unless otherwise indicated, all numbers expressing quantities of components, conditions, and so forth used in the specification and claims are to be understood as being modified in all instances by the term "about". Accordingly, unless indicated to the contrary, the numerical parameters set forth in the instant specification and attached claims are approximations that can vary depending upon the desired properties sought to be obtained by the presently disclosed subject matter.

As used herein, the term "about", when referring to a value or to an amount of mass, weight, time, volume, concentration, and/or percentage can encompass variations of, in some embodiments +/−20%, in some embodiments +/−10%, in some embodiments +/−5%, in some embodiments +/−1%, in some embodiments +/−0.5%, and in some embodiments +/−0.1%, from the specified amount, as such variations are appropriate in the disclosed packages and methods.

As used herein, the term "and/or" includes any and all combinations of one or more of the associated listed items.

Relative terms such as "below" or "above" or "upper" or "lower" or "horizontal" or "vertical" may be used herein to describe a relationship of one element, layer, or region to another element, layer, or region as illustrated in the drawing figures. It will be understood that these terms and those discussed above are intended to encompass different orientations of the device in addition to the orientation depicted in the drawing figures.

The embodiments set forth below represent the necessary information to enable those skilled in the art to practice the embodiments and illustrate the best mode of practicing the embodiments. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

FIG. 1 illustrates one embodiment of a vein introducer and/or cannulation needle in accordance with some embodiments of the presently disclosed subject matter. The term "introducer" refers to a needle used for placing a catheter or other device into a blood vessel. The term "cannulation" refers to a procedure in which a cannula is inserted into a blood vessel by puncturing the skin and venipuncturing the blood vessel wall. Thus, the distal end of the cannula is disposed in the blood vessel and the proximal end of the cannula is disposed on the outside of the body part. As shown in FIG. 1, needle 5 is configured to be at least partially non-linear. Specifically, the needle includes optional straight section 10 attached a distal end of housing 15, and curved section 20 that comprises sharp tip 25. The disclosed needle can be used to provide fluidic and/or instrument access to an internal body structure (e.g., a subclavian vein), as disclosed in more detail below.

Figure 2A:
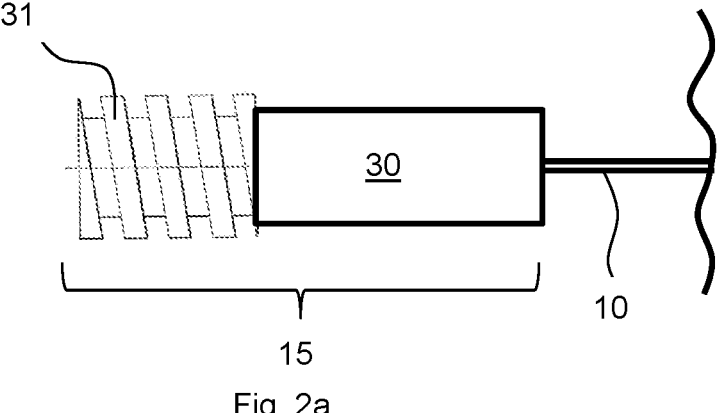
FIG. 2a is a side plan view of a needle housing in accordance with some embodiments of the presently disclosed subject matter.

FIG. 2a illustrates one embodiment of needle housing 15. The term "needle housing" refers to any coupling element that allows the needle to be attached to a medical device or instrument, such as (but not limited to) a syringe, IV line, and the like. To this end, the housing can include body 30 and one or more connectors 31 that allow the needle to be releasably or permanently coupled to a medical device or instrument. For example, the housing can be coupled to a conduit for conveying fluids to and/or from the disclosed needle and/or a container (such a blood collection vial).

Connector 31 can comprise one or more screw threads, pressure-fit closures, magnets, snap-fit closures, clips, fasteners, or any other element that allows the housing to be coupled to another component, acting as a fitting. It should be appreciated that the connector can be positioned at the proximate end of the housing, as shown in FIG. 2a.

Figure 2B:
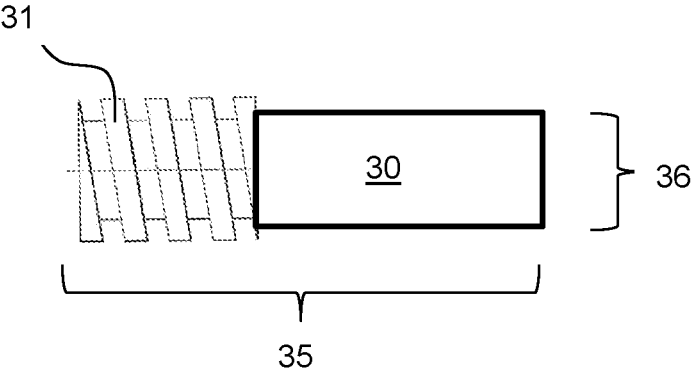
FIG. 2b is a side plan view of a needle housing depicting a length and width in accordance with some embodiments of the presently disclosed subject matter.
Figure 2C:
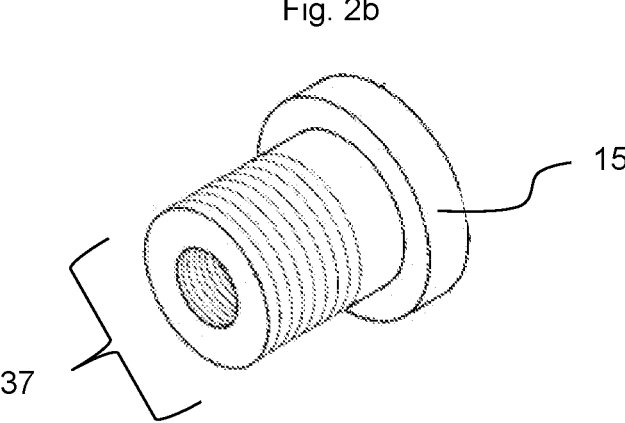
FIG. 2c is a perspective view of a needle housing in accordance with some embodiments of the presently disclosed subject matter.

Housing 15 can comprise any desired length 35. The term "length" refers to the longest horizontal distance from the proximate end to the distal end of the housing. For example, in some embodiment the housing can have a length of about 0.1-2 inches (e.g., at least/no more than about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, or 2 inches), as shown in FIG. 2b. The housing can further include width 36 of about 0.1-0.5 inches (at least/no more than about 0.1, 0.2, 0.3, 0.4, 0.5 inches). The term "width" refers to the longest horizontal distance perpendicular to the length. The housing can also include thickness 37 of about 0.1-0.5 inches, as illustrated in FIG. 2c. The term "thickness" refers to the longest horizontal distance perpendicular to both the length and width. It should be appreciated that the length, width, and thickness of the housing are not limited and can be configured outside the ranges given herein.

Housing 15 can be constructed from any desired material, such as (but not limited to) plastic, metal, ceramics, and the like.

Figure 3A:
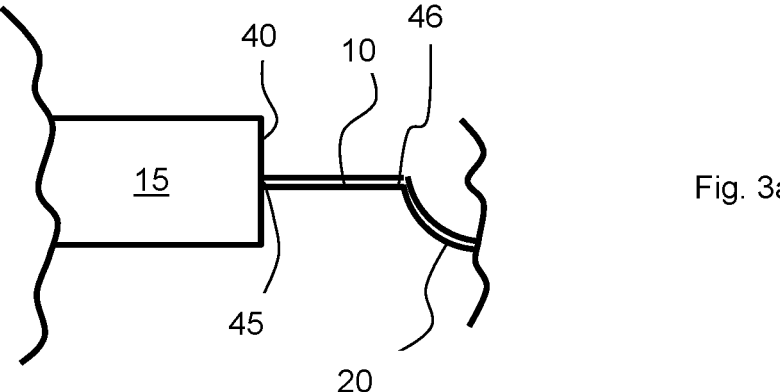
FIG. 3a is a cross-sectional side plan view of a needle straight section in accordance with some embodiments of the presently disclosed subject matter.

Distal end 40 of the housing is joined to straight section 10, as shown in FIG. 3a. Particularly, proximal end 45 of the straight section is coupled to the housing, while straight section distal end 46 is attached to curved section 20. The term "straight" refers to the portion of needle 5 that is linear (e.g., no concave or convex surfaces) between proximal and distal ends 45, 46.

Figure 3B:
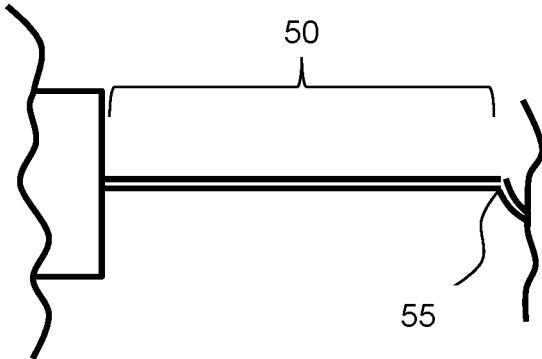
FIG. 3b is a cross-sectional side plan view of a needle straight section illustrating a length in accordance with some embodiments of the presently disclosed subject matter.

Straight section 10 of needle 5 can have any suitable length 50, as illustrated in FIG. 3b. For example, length 50 can be about 0.1-1 inches in some embodiments. Thus, the length of straight section 10 can be at least about (or no more than about) 0.1, 0.2, 0.3, 0.4, 0.5, 0.6, 0.7, 0.8, 0.9, or 1 inch. However, the presently disclosed subject matter is not limited and length 50 can be configured outside the range given above.

As set forth above, needle 5 further includes curved section 20 attached to the distal end of straight section 10. The needle straight and curved sections 10, 20 of the needle join at transition point 55, as shown in FIG. 3b.

Figure 3C:
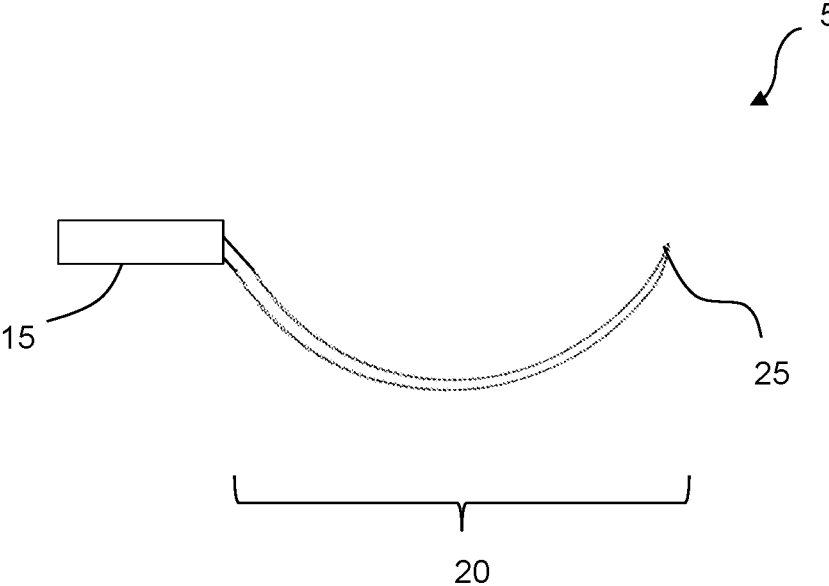
FIG. 3c is a side plan view of a needle configured without a straight section in accordance with some embodiments of the presently disclosed subject matter.

However, it should be appreciated that straight section 10 is optional and needle 5 can be configured without this element, as illustrated in FIG. 3c. In such embodiments, housing 15 is directly joined to curved section 20 at transition point 56.

Figure 4A:
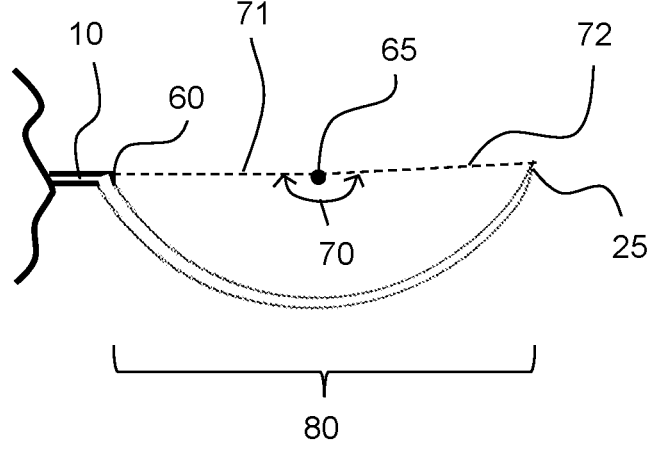
FIG. 4a is a cross-sectional side plan view of a needle curved section in accordance with some embodiments of the presently disclosed subject matter.

FIG. 4a illustrates one embodiment of needle curved section 20 formed in a circular arc shape (e.g., shape of the letter "C"). The term "curved" refers to a structure having at least one concave or convex surface along the body between proximal end 60 and sharp distal tip 25. The curved section includes a rounded or arched shape around a virtual curvature center 65. The "virtual curvature center" refers the midway point between a straight line drawn from the distal end to the proximal end of the curved section. First and second straight lines 71, 72 are drawn from the virtual curvature center to the proximal and distal ends. Central angle 70 represents the angle of curvature between lines 71, 72. The central angle 70 of the curved section can be configured such that tip 25 can enter the body and pass into a blood vessel (e.g., the subclavian vein). Thus, in some embodiments, central angle 70 can be about 150-270 degrees (e.g., at least/no more than about 150, 155, 160, 165, 170, 175, 180, 185, 190, 195, 200, 205, 210, 215, 220, 225, 230,235, 240, 245, 250, 255, 260, 265, or 270 degrees. Importantly, the curved section allows tip 25 to advance along the long axis of the vein, and not in the direction of the vessel wall inferiorly, superiorly, laterally, or medially (short axis of the vein), as set forth in more detail below.

Curved section 20 comprises length 80 that spans the distance between the distal and proximal ends. Curved section 30 can have any suitable length, such as about 0.1-5 inches. Thus, length 80 can be at least about (or no more than about) 0.1, 0.25, 0.5, 0.75, 1, 1.25, 1.5, 1.75, 2, 2.25, 2.5, 2.75, 3, 3.25, 3.5, 3.75, 4, 4.25, 4.5, 4.75, or 5 inches. However, the length of curved segment 20 can be outside the given range and is not limited.

Figure 4D:
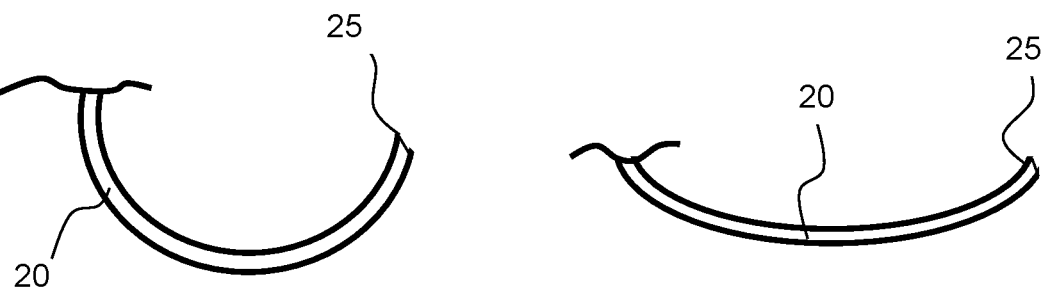
FIG. 4d is a cross-sectional side plan view a parabolic curved needle section in accordance with some embodiments of the presently disclosed subject matter.
Figure 4D:
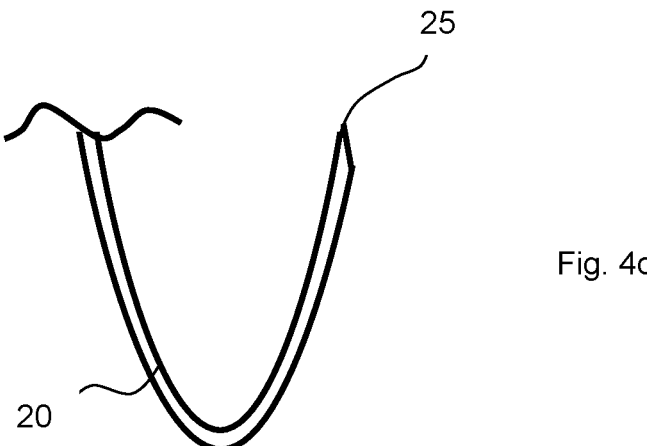

It should be appreciated that the shape of curved section 20 can vary. In some embodiments, the shape can be a segment of a circle, a segment of an ellipse, or a segment of a parabola, as shown in FIGS. 4b-4d, respectively. The shape can further vary from any of these forms. As discussed below, the curved section allows penetration of tissue in a curved manner.

Figure 5:
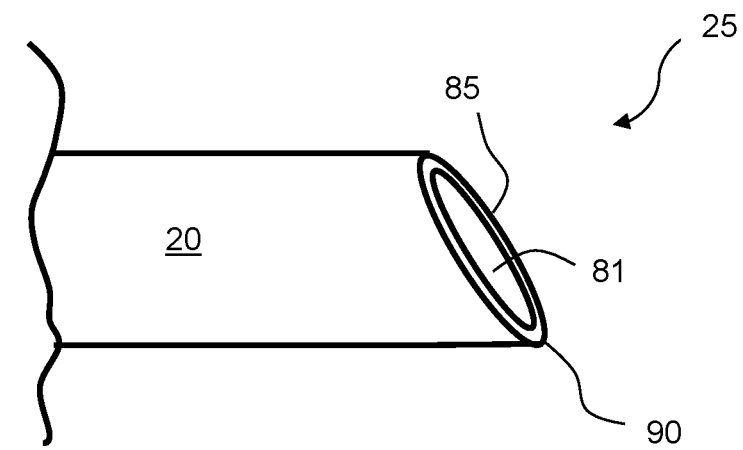
FIG. 5 is a fragmentary view of a needle tip in accordance with some embodiments of the presently disclosed subject matter.

Needle tip 25 is configured at the distal end of curved section 20. The needle tip can be constructed as a conventional sharp tip with open orifice 81 that extends into the interior of the needle from angled edge 85, as shown in FIG. 5. The tip includes distal point 90 that is sharp and/or angled to enable piecing of the patient's skin layer and vascular wall with minimal discomfort to the patient.

Figure 6:
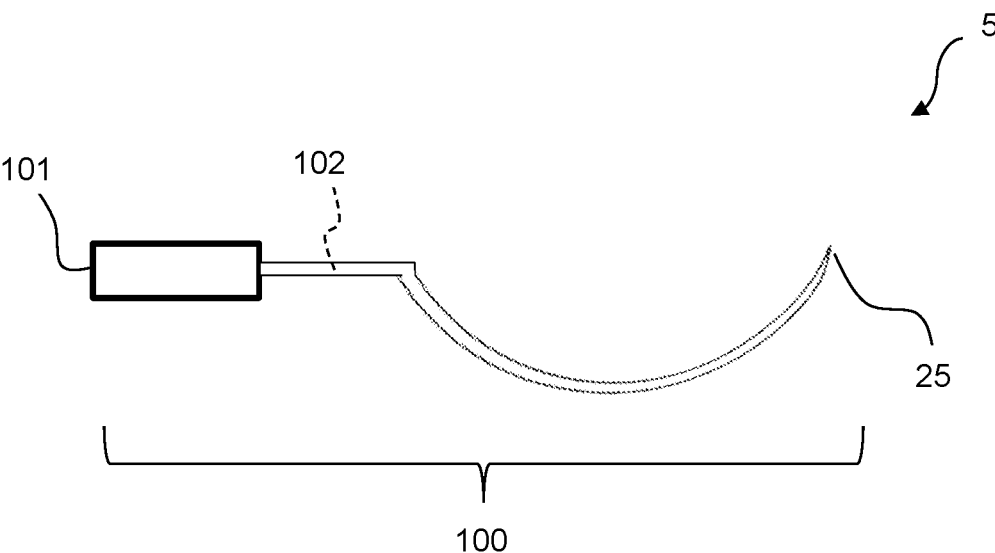
FIG. 6 is a cross-sectional side view of a needle in accordance with some embodiments of the presently disclosed subject matter.

The total length of needle 5 can vary depending on the intended use. For example, total length 100 can be about 0.25-5 inches in some embodiments, as illustrated in FIG. 6. Thus, length 100 can be at least about (or no more than about) 0.25, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, or 5 inches. The term "total length" refers to the distance from the needle proximal end 101 to the distal end (tip 25).

In some embodiments, curved section 20 makes up about 40-90 percent of the total length of the needle (e.g., at least/no more than about 40, 45, 50, 55, 60, 65, 70, 75, 80, 85, or 90 percent). The straight section can make up about 5-50 percent of the total length of the needle (e.g., at least/no more than about 5, 10, 15, 20, 25, 30, 35, 40, 45, or 50 percent). Housing 15 can make up about 5-50 percent of the total length of the needle (e.g., at least/no more than about 5, 10, 15, 20, 25, 30, 35, 40, 45, or 50 percent).

Figure 7A:
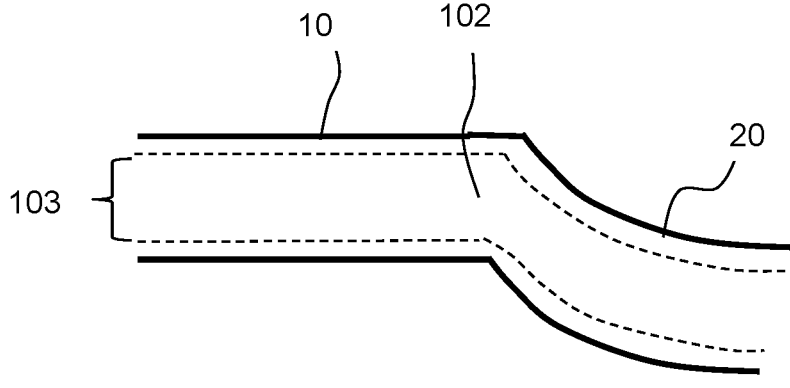
FIG. 7a is a cross-sectional view illustrating a needle internal channel in accordance with some embodiments of the presently disclosed subject matter.
Figure 7B:
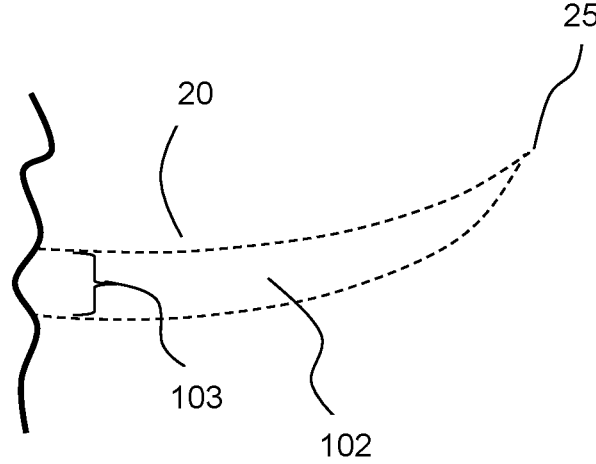
FIG. 7b is a cross-sectional view illustrating a tapered internal channel in accordance with some embodiments of the presently disclosed subject matter.
Figure 8A:
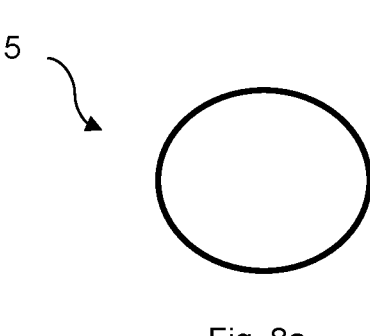
FIGS. 8a-8f illustrate circular, oval, square, rectangular, triangular, and pentagonal cross-sectional views of a needle in accordance with some embodiments of the presently disclosed subject matter.
Figure 8B:
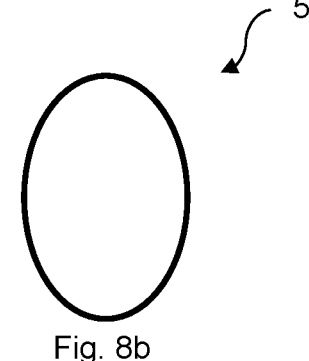
Figure 8C:
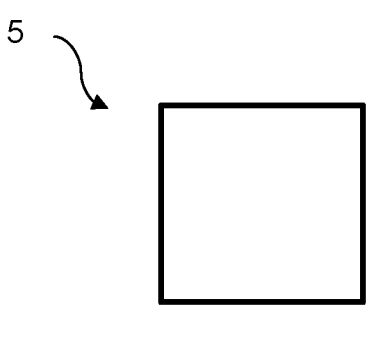
Figure 8D:
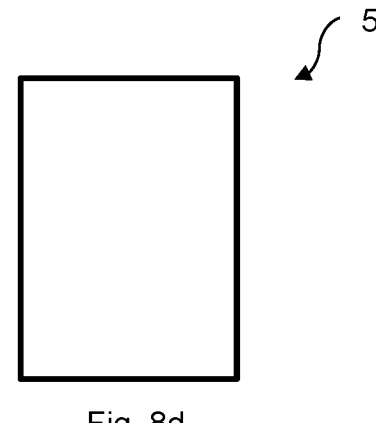
Figure 8E:
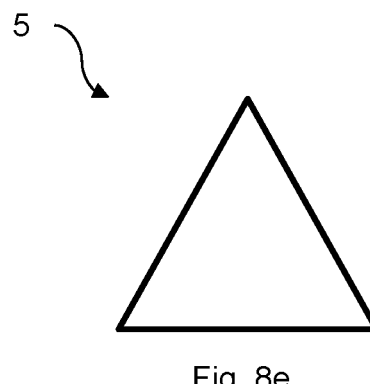
Figure 8F:
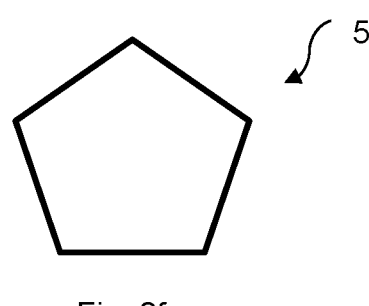

As set forth above, needle 5 is tubular in structure. As such, the needle includes internal channel 102 that acts as a passageway. Thus, the housing, straight section, and curved section are all in fluid communication via channel 102. In some embodiments, the internal channel of the needle has a constant diameter 103 through the straight and curved sections as shown in FIG. 7a. For example, the diameter can be about 0.1-1 mm. In other embodiments, the distal end of the needle (towards tip 25) can taper in diameter 103 to provide some supporting force at the proximal end, as shown in FIG. 7b. The tapered portion of the needle can range from about 0.05-0.5 mm (e.g., at least/no more than about 0.05, 0.1, 0.2, 0.3, 0.4, or 0.5 mm).

The straight and curved sections of needle 5 can be constructed from any of a wide variety of suitable materials. For example, the sections can be constructed from stainless steel, nitinol, tantalum, cobalt, chrome, titanium, nickel, and/or combinations or alloys thereof. In some embodiments, the materials used to construct sections 10, 20 are biocompatible. The term "biocompatible" refers to a material that is substantially non-toxic in the in vivo environment of its intended use.

In some embodiments, the needle is constructed from one or more sterilizable materials. The term "sterilizable" refers to the capability to withstand sterilization treatment performed using standard techniques (e.g., autoclave, dry heat sterilization, formalin gas, ozone gas, gamma radiation, and the like). In other embodiments, needle 5 is disposable and can be recycled or discarded after each use.

Needle 5 can have any desired cross-sectional shape, such as (but not limited to) circular, oval, square, rectangular, triangular, pentagonal, and the like, as shown in FIGS. 8a-8f. However, it should be appreciated that the disclosed needle is not limited and can be configured in any desired cross-sectional shape.

Needle 5 can be formed using any conventional method or system. For example, the straight and curved sections can be permanently attached through welding or other methods. In other embodiments, the straight and curved sections are formed as a single unit. Housing 15 can be attached to the proximal end of the straight section using any suitable mechanism, such as the use of adhesives, welding, the like.

Figure 9:
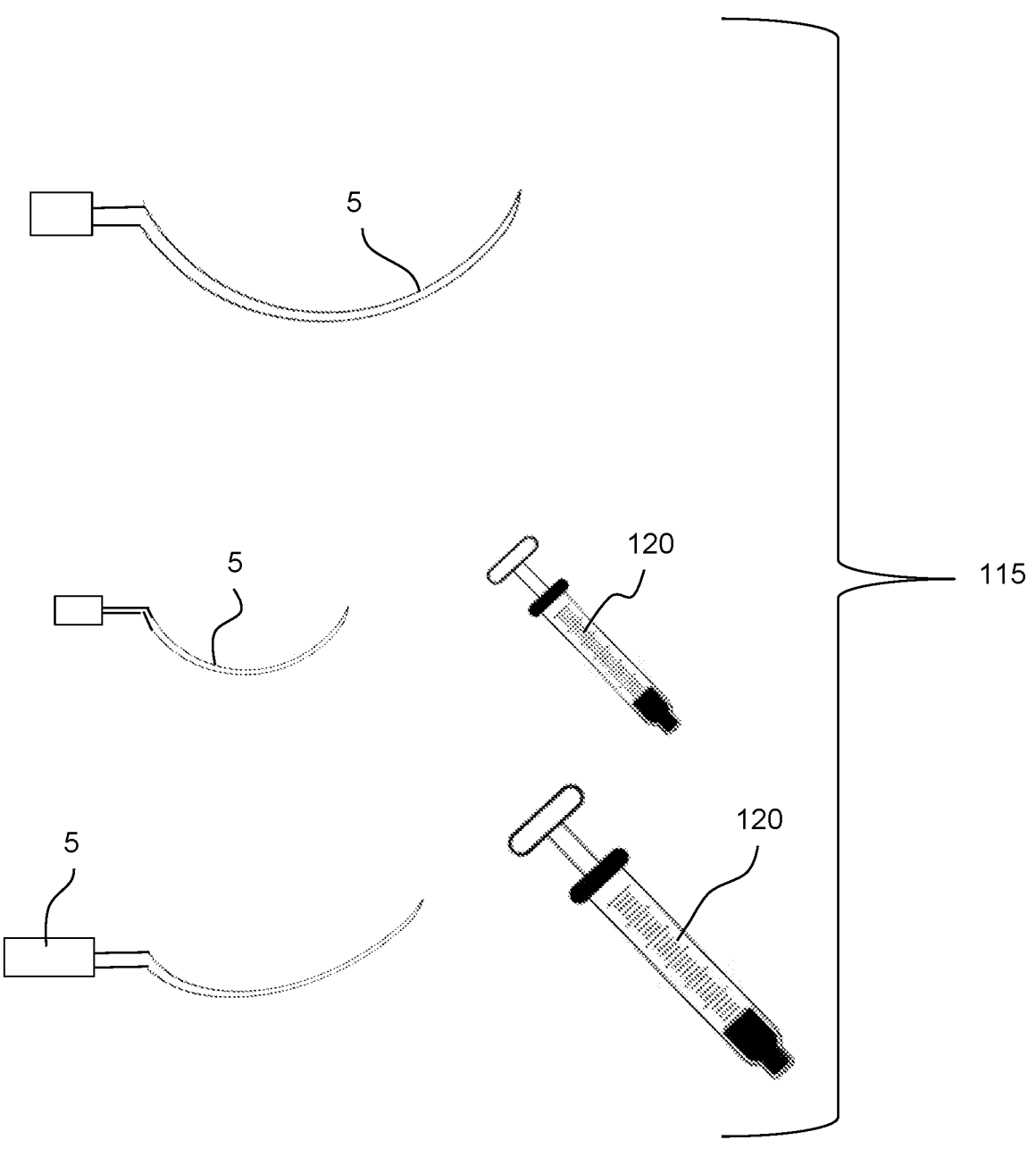
FIG. 9 is an illustration of a representative kit in accordance with some embodiments of the presently disclosed subject matter.

In some embodiments, the presently disclosed subject matter includes kit 115 comprising a plurality of sizes and/or shapes of needle 5. One or more accessories 120 (e.g., guides, cannulas, and other devices) can also be included, as illustrated in FIG. 9. A user can select an appropriate needle and/or accessory based on an anticipated use and/or the patient's particular characteristics.

Figure 10A:
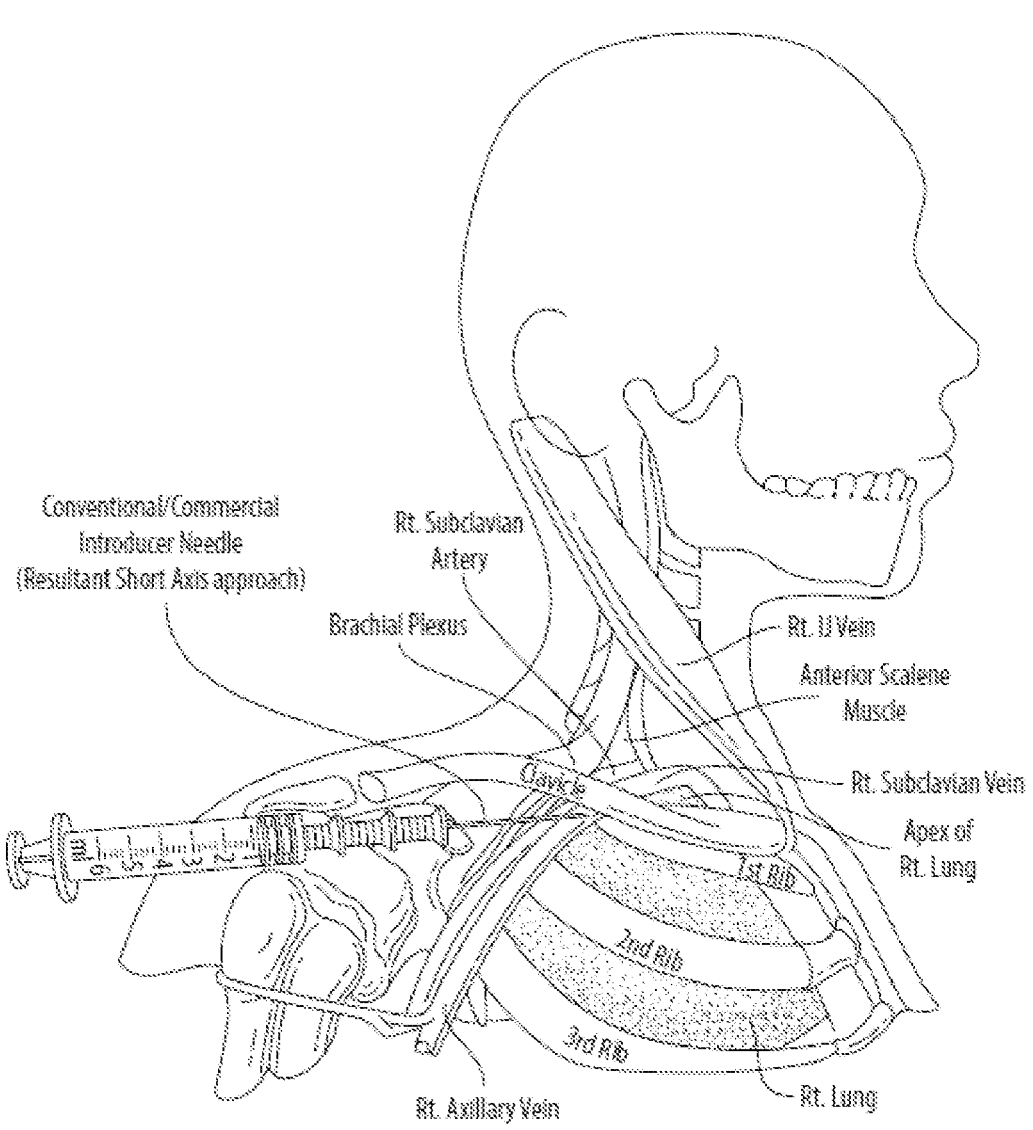
FIG. 10a is a perspective view of a conventional needle positioned adjacent to a subclavian vein.

In use, needle 5 can be used to access a desired blood vessel. For example, FIG. 10a illustrates conventional needle 130 comprising linear tip 25. As shown, lung 135, subclavian artery 140, brachial plexus 145, first rib 150, anterior scalene muscle 155, and right internal jugular vein 160 are positioned very close to subclavian vein 165 throughout its course. Accordingly, if a conventional straight needle is inserted too far into the body and/or at an incorrect angle, it can easily puncture the lung or other nearby structure.

Figure 10B:
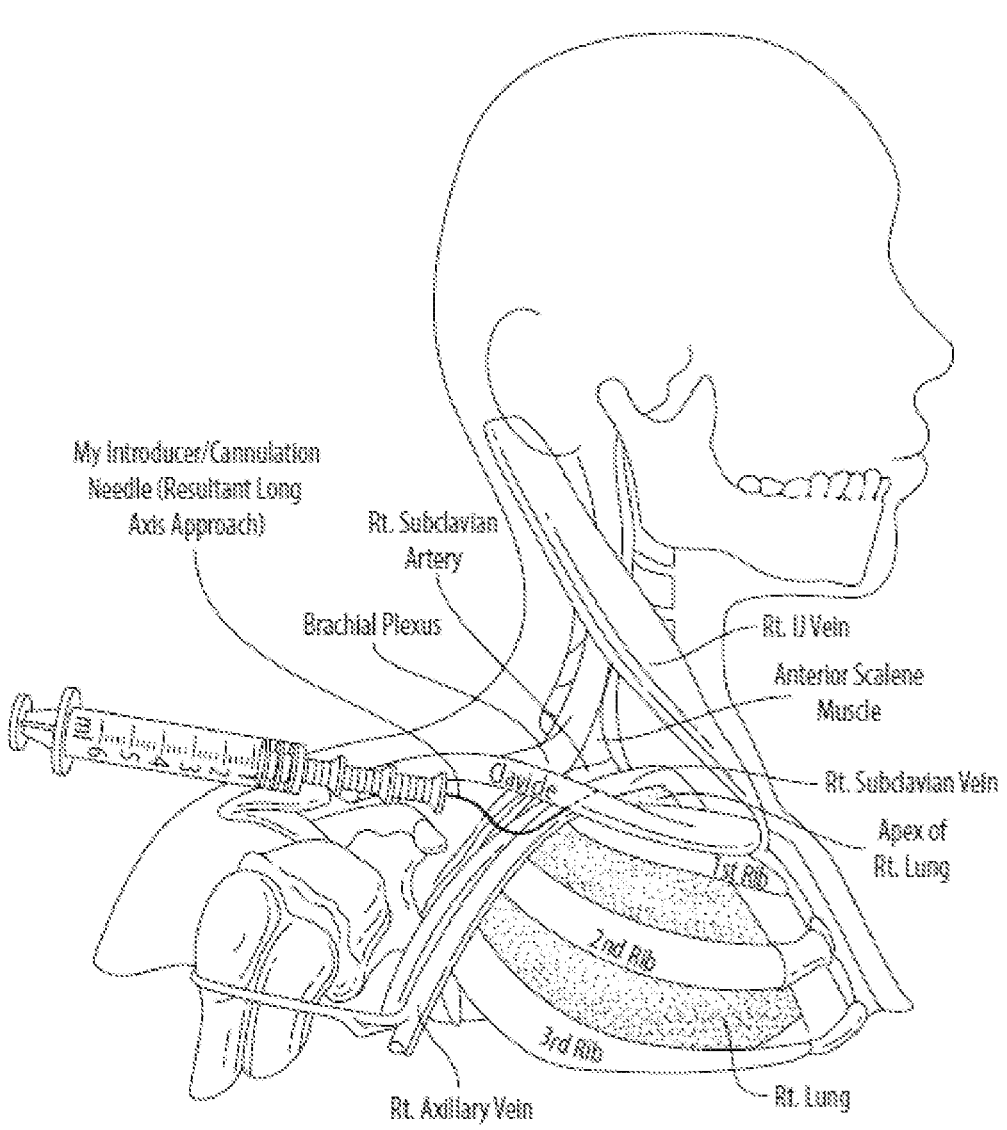
FIG. 10b is a perspective view of a curved needle positioned adjacent to a subclavian vein in accordance with some embodiments of the presently disclosed subject matter.

However, disclosed needle 5 is sized and shaped to be easily and safely inserted into a desired vessel (e.g., the subclavian vein), as shown in FIG. 10b. Specifically, the needle includes housing 15 and tubular straight and curved segments 10, 20 extending distally from the housing. In use, needle 5 is configured such that sharp tip 25 is urged into the tissue overlying the subclavian vein. The curved section of the needle can be advanced substantially parallel (e.g., along the long axis) to the vein. When fully inserted, the curved tip of the needle can be positioned within the vein while at least a portion of curved section 20 is outside the vein. The straight section of the needle can extend through the skin surface, through the tissue overlaying the vein. The straight section and/or housing can be used to stabilize the needle relative to the patient.

Figure 10C:
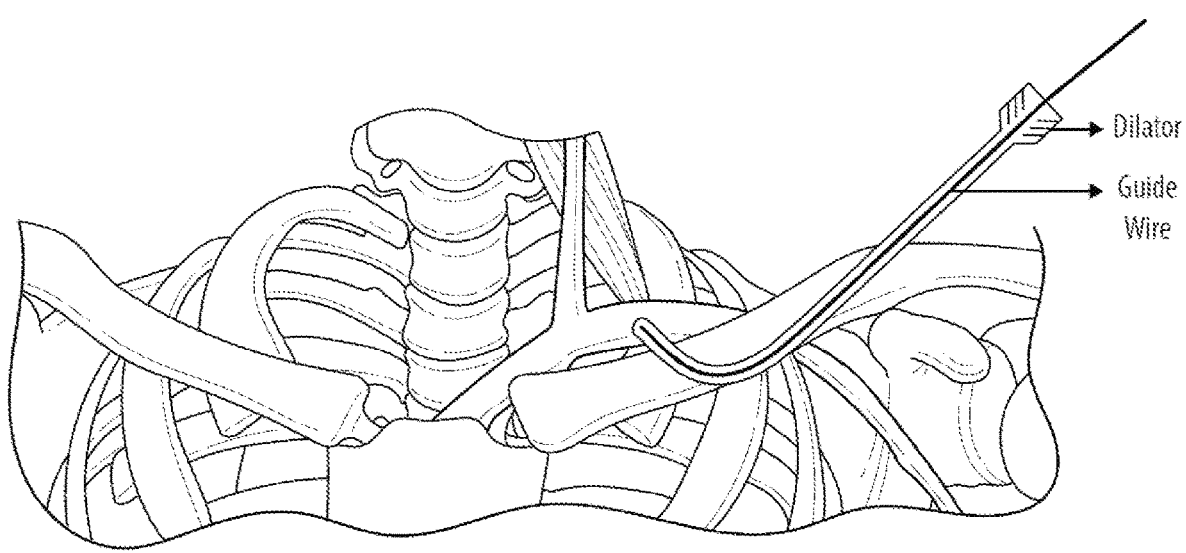
FIG. 10c is a perspective view of a dilator and guidewire within the tissue of a patient in accordance with some embodiments of the presently disclosed subject matter.

As the curved subclavian vein needle is hugging the inferior half of the clavicle and entering the subclavian vein from its inferior aspect, the guide wire within the subclavian vein after the withdrawal of the needle is also in a curved fashion from the skin to its entry into the subclavian vein. Thus, we a user is dilating the track with dilators provided, they should envision this slightly curved course of the guidewire within the tissue and advance the dilators along this course of the guidewire, as shown in FIG. 10c.

In one specific example, needle 5 can be used as a subclavian vein introducer and/or cannulation needle. Humans have a pair of subclavian veins located in the upper chest region, one on each side, as shown in FIG. 10b. Each subclavian vein is a continuation of the axillary vein, that runs underneath the clavicle, curves and joins the Internal Jugular Vein (IJV) to form the Innominate vein. The innominate vein combines with its counterpart to form the superior vena cava that enters the heart. The subclavian vein is a very useful vein for central venous access for a variety of reasons. For example, it provides a lowered risk of infection and thrombosis compared to other veins. In addition, it maintains patency in shock, has easy accessibility and maintenance, and provides increased patient comfort.

In some embodiments, the presently disclosed subject matter is directed to a method of treating a patient in need thereof. The method includes locating a target site of treatment in the patient. The disclosed needle is then adjusted such that it is positioned relative to the patient at the site and orientation to allow access to the patient's subclavian vein. Tip 25 of needle 5 is inserted at the target site, and the needle is maneuvered inside the patient using the curved section proximate to the distal end to facilitate placement within the target vessel. Once the needle tip has been inserted into the vein, the individual can be treated as desired by the user. The needle can be used to add a fluid, substance, and/or instrument to the vessel. In other embodiments, the needle, can be used to remove a substance (e.g., blood) from a vessel. After treatment, the needle is simply removed from the patient and discarded or disposed of.

The disclosed system includes many advantages of the prior art. Particularly, needle 5 can be used to provide access with respect to an internal body structure, such as (but not limited to) a subclavian vein.

Advantageously, the size and shape of needle 5 enhances the success rate for successful cannulation (introducing a cannula or thin tube into a vein).

Needle 5 further avoids complications common with straight needles, such as pneumothorax (collapsed lung) and hemothorax (presence of blood in the pleural space).

The disclosed needle has a success rate for cannulation of over 80% and a complication rate of 0-1%. The complication rate for conventional needle is 5-10% and the success rate is about 50-60%.

The curved section gives needle 5 a significant advantage over conventional straight needles that have a limited range of movement. Because of this additional range of movement, the curved needle can be easily inserted into a vessel, while avoiding additional discomfort and risks to the patient, which include complications from leakage of cement or inadvertent infusion into non-target areas.

Needle 5 can be used on a wide variety of patients. The term "patient" refers to humans, as well as animals for veterinary use.

As described above, although a preferred embodiment of the present invention has been described for illustrative purposes, those skilled in the art will appreciate that various modifications, additions and substitutions are possible, without departing from the scope and spirit of the invention as disclosed in the accompanying claims.

EXAMPLES

The following Examples provide illustrative embodiments. In light of the present disclosure and the general level of skill in the art, those of ordinary skill in the art will appreciate that the following Examples are intended to be exemplary only and that numerous changes, modifications, and alterations can be employed without departing from the scope of the presently disclosed subject matter.

What is claimed is:

1. A tubular needle comprising:

a housing defined by a housing proximal end and a housing distal end, wherein the housing proximal end includes a connector;

a straight section comprising a proximal end and a distal end, the proximal end of the straight section operably connected to the housing distal end;

a curved section comprising a proximal end and a distal end, wherein the proximal end of the curved section is operably connected to the distal end of the straight section, and wherein the distal end of the curved section comprises a sharpened tip;

wherein the curved section comprises a central angle of about 150 degrees to about 270 degrees, is configured as a segment of a circle, and forms a substantially C-shaped or U-shaped configuration.

2. The tubular needle of claim 1, wherein the connector comprises a series of screw threads.

3. The tubular needle of claim 1, wherein the straight section has a length of about 0.1-1 inches and the curved section has a length of about 0.1-5 inches.

4. The tubular needle of claim 1, wherein the curved section comprises about 40-90 percent of a total length of the tubular needle, the straight section comprises as about 5-50 percent of the total length of the tubular needle, and the housing comprises about 5-50 percent of the total length of the tubular needle.

5. The tubular needle of claim 1, configured within a kit comprising a plurality of tubular needles of various sizes and shapes.

6. The tubular needle of claim 1, wherein the straight section, curved section, or both are constructed from stainless steel, nitinol, tantalum, cobalt, chrome, titanium, nickel, and/or combinations or alloys thereof.

7. The tubular needle of claim 1, wherein the curved section is defined about a center point from which the curved section extends.

8. The tubular needle of claim 1, wherein the tubular needle comprises an internal channel having a constant diameter through the straight section and the curved section.

9. The tubular needle of claim 1, wherein the tubular needle comprises an internal channel that tapers toward the sharpened tip.

10. A method of accessing a target vessel, the method comprising:

positioning the tubular needle of claim 1 at a target location on a patient;

advancing the sharpened tip of the tubular needle of claim 1 into the interior of the patient;

maneuvering the curved section of the tubular needle of claim 1 inside the patient to facilitate placement along the long axis of the target vessel;

whereby the target vessel is accessed.

11. The method of claim 10, wherein the target vessel is a subclavian vein.

12. The method of claim 10, wherein the target vessel is accessed to withdraw blood, place a central venous catheter, administer fluids, administer medication, monitor blood pressure, perform hemodialysis, insert a medical device, or combinations thereof.

13. A method of treating a patient by accessing a target vessel, the method comprising:

positioning the tubular needle of claim 1 at a target location on the patient;

advancing the sharpened tip of the tubular needle of claim 1 into the interior of the patient;

maneuvering the curved section of the tubular needle of claim 1 inside the patient to facilitate placement along the long axis of the target vessel;

wherein the patient is treated by accessing the target vessel.

14. The method of claim 13, wherein the target vessel is a subclavian vein.

15. The method of claim 13, wherein the treating comprises withdrawing blood, inserting a central venous catheter, administering fluids, administering medication, monitoring blood pressure, performing hemodialysis, inserting a medical device, or combinations thereof.

\*    \*    \*    \*    \*